(12) United States Patent
Resnick et al.

(10) Patent No.: US 8,414,872 B2
(45) Date of Patent: Apr. 9, 2013

(54) HAIR STRAIGHTENING FORMULATIONS, METHODS AND SYSTEMS

(75) Inventors: Lionel Resnick, Weston, FL (US); Irwin Grams, Boca Raton, FL (US); Angela Goodfellow, Ottawa (CA); David Allice, Toronto (CA)

(73) Assignee: Liquid Keratin, Inc., Ottawa (CA)

( * ) Notice: Subject to any disclaimer, the term of this patent is extended or adjusted under 35 U.S.C. 154(b) by 963 days.

(21) Appl. No.: 12/206,374

(22) Filed: Sep. 8, 2008

(65) Prior Publication Data

US 2009/0165812 A1 Jul. 2, 2009

Related U.S. Application Data

(60) Provisional application No. 60/971,001, filed on Sep. 10, 2007.

(51) Int. Cl.
*A61Q 5/04* (2006.01)
(52) U.S. Cl. ........ 424/70.2; 132/202
(58) Field of Classification Search ............ None
See application file for complete search history.

(56) References Cited

U.S. PATENT DOCUMENTS

| | | | |
|---|---|---|---|
| 4,148,329 A | 4/1979 | Jaskowski | |
| 4,304,244 A | 12/1981 | de la Guardia | |
| 4,591,497 A | 5/1986 | Naito | |
| 4,806,595 A | 2/1989 | Noishiki | |
| 4,898,726 A | 2/1990 | Beste | |
| 4,911,919 A | 3/1990 | Patel | |
| 5,080,670 A | 1/1992 | Imamura | |
| 5,639,449 A | 6/1997 | Syed | |
| 5,641,478 A | 6/1997 | Syed | |
| 5,679,327 A | 10/1997 | Darkwa | |
| 5,753,214 A | 5/1998 | Yoshioka | |
| 6,007,585 A * | 12/1999 | Syed et al. ............ | 8/432 |
| 6,284,230 B1 | 9/2001 | Sako | |
| 6,306,805 B1 * | 10/2001 | Bratescu et al. ........ | 510/123 |
| 6,376,455 B1 | 4/2002 | Friedli | |
| 6,491,933 B2 | 12/2002 | Lorenzi | |
| 6,494,920 B1 | 12/2002 | Weuthen | |
| 6,555,505 B1 | 4/2003 | King | |
| 6,596,035 B2 | 7/2003 | Gutkowski | |
| 6,602,493 B2 | 8/2003 | Akhter | |
| 6,610,280 B2 | 8/2003 | Ainger | |
| 6,696,067 B2 | 2/2004 | Brandt | |
| 6,709,648 B2 * | 3/2004 | Sako et al. ............. | 424/70.12 |
| 6,805,136 B2 | 10/2004 | Browning | |
| 6,994,846 B2 | 2/2006 | L'Alloret | |
| 7,025,955 B2 | 4/2006 | Siddiqui | |
| 7,105,184 B2 | 9/2006 | Pauly | |
| 7,148,327 B2 | 12/2006 | Kelly | |
| 7,250,174 B2 | 7/2007 | Lee | |
| 7,318,929 B2 | 1/2008 | Schieferstein | |
| 7,390,468 B2 | 6/2008 | Pekkala | |
| 7,390,478 B2 | 6/2008 | Akyuz | |
| 7,867,478 B2 * | 1/2011 | Nicolas-Morgantini et al. ............ | 424/70.2 |
| 2002/0182161 A1 | 12/2002 | Ainger | |
| 2003/0003070 A1 | 1/2003 | Eggers | |
| 2003/0235554 A1 | 12/2003 | Chahal | |
| 2004/0052748 A1 | 3/2004 | Vondruska | |
| 2004/0105836 A1 | 6/2004 | Seipel | |
| 2005/0186164 A1 | 8/2005 | Akyuz | |
| 2005/0201967 A1 | 9/2005 | Albrecht | |
| 2006/0057090 A1 | 3/2006 | Buchwald-Werner | |
| 2006/0104928 A1 | 5/2006 | Furtado | |
| 2006/0165635 A1 | 7/2006 | Kelly | |
| 2006/0183662 A1 | 8/2006 | Crotty | |
| 2006/0194760 A1 | 8/2006 | Griesbach | |
| 2006/0251602 A1 | 11/2006 | Goddinger | |
| 2007/0048235 A1 | 3/2007 | Harmalker | |
| 2007/0185281 A1 | 8/2007 | Song | |
| 2007/0202069 A1 | 8/2007 | Tamaeselvy | |
| 2007/0207097 A1 | 9/2007 | Kelly | |
| 2008/0004423 A1 | 1/2008 | Kelly | |

FOREIGN PATENT DOCUMENTS

| | | |
|---|---|---|
| DE | 102004002168 A1 | 8/2005 |
| WO | WO2007032762 | 3/2007 |

* cited by examiner

*Primary Examiner* — Jyothsna Venkat
(74) *Attorney, Agent, or Firm* — Cowan, Liebowitz & Latman, P.C.

(57) ABSTRACT

The present invention includes a hair straightening formulation consisting of a hair fixative that will straighten the hair for at least 2-3 months after one application despite frequent washings of the hair as well as methods for obtaining said formulation. The formulation comprises as active ingredients one or more keratin hydrolysates and an aldehyde. Hair straightening system comprising shampoo and one or more conditioners are also provided. The invention is further directed to a method for straightening hair using said formulation.

4 Claims, No Drawings

HAIR STRAIGHTENING FORMULATIONS, METHODS AND SYSTEMS

PRIORITY CLAIM

This application claims the benefit of provisional application Ser. No. 60/971,001, filed Sep. 10, 2007 under 35 USC 119(e), the contents of which are incorporated herein by reference.

FIELD

One or more hair straightening formulations are provided to straighten the hair for at least 2-3 months after one application despite frequent washings of the hair. One or more hair straightening systems comprising said formulation as well as one or more shampoos and one or more conditioners are provided. In addition, one or more methods for straightening hair using said formulations and systems are provided.

BACKGROUND

Human hair has many textures, from fine to coarse and from straight to curly. Hair is made of keratin which in turn is made of polypeptide chains bonded together by cysteine (or disulfide) bonds, hydrogen bonds and salt linkages.

Curly hair is made of hair strands that have irregular surfaces that mesh and tangle with each other to make combing more difficult. Among individuals with very curly hair, e.g., individuals of African or Middle Eastern descent, it is especially popular to relax or straighten hair to increase hair manageability and ease of styling. Threads are composed of proteins of spiral structures, linked by a sulfur double-bond. These bonds are responsible for the hair structure and they may be broken by certain reduction reactions. The most common reductive agents are thioglycolic acid and its derivatives such as ammonium thioglycolate and bisulfite. These act on the hair keratin by breaking disulfide bonds that link cysteine units; this way, they form cysteine, the main component of keratin. The hair to be relaxed is exposed to a relaxer that chemically transforms cysteine bonds of the hair to lanthionine bonds. For this reason, the term for the chemical relaxing process is lanthionization.

Hair straightening or hair relaxing products have been commercially available for over forty years for people who want straighter and more manageable hair. Most commercially available hair relaxers are composed of a strong hydroxide base that breaks the bonds in the hair. The first straightening chemicals were developed around 1940. They were rudimental preparations of sodium or potassium hydroxide blended with starch and they were highly irritating to the scalp. By the 1950s, several kits for chemical straightening, based on sodium hydroxide, were introduced in the professional market. In 1965, the market already had a chemical straightening product for home use, based on sulfites. In 1985, Avon Industries introduced a straightening system based on types of hair and scalp sensitivity (i.e., normal and sensitive). The first one used sodium hydroxide as its active ingredient and the other used guanidine hydroxide. However, the results provided by existing straightening products are not optimal; nor is their safety. Current products present inconvenience issues, such as weakening of threads, irritation of the scalp and difficulty in rinsing. Also due to their instability, these formulations degrade rapidly.

SUMMARY

One or more hair straightening formulations are provided. These hair straightening formulations comprise as active ingredients: (a) one or more keratin cross-linking agents and (b) one or more keratin protein fractions. In a particular embodiment, the keratin cross-linking agent comprises a nonformaldehyde aldehyde, more particularly a dialdehyde and even more particularly, glyoxal. The hair straightening formulations may be in the form of lotion, cream, gel, spray, foam, ointment, shampoo, conditioner, aerosol, mousse or liquid suspension in a sponge or other applicator.

In certain advantageous embodiments, the hair straightening formulations are guanidinium, formaldehyde, paraben and lye free. In a specific embodiment, the hair straightening formulations comprise (a) one or more dialdehydes; (b) one or more keratin protein fractions and optionally (c) at least one of (i) one or more surfactants; (ii) one or more emollients; (iii) one or more emulsifiers; (iv) one or more preservatives, (v) one or more skin protecting agents and (v) one or more diluents.

In a particular embodiment, the formulations comprise each of the components in the following amounts:

| substance | % By Weight |
| --- | --- |
| Dialdehyde | 0.05-10% |
| Keratin | 0.05-15% |
| Surfactant | 0.1-15% |
| Emollient | 0.1-15% |
| Emulsifier | 0.1-15% |
| Preservative | 0.1-5% |
| Diluent | 0.1-5% |
| Skin protecting agent | 0.1-10% |

The formulations may also comprise one or more thickeners, fragrances and/or sunscreen agents.

In yet a more specific embodiment, the hair straightening formulations comprise glyoxal, hydrolyzed keratin, one or more silicone containing emollients, one or more polyoxy ethers of lauryl alcohol, one or more glycerin compounds, one or more skin cleansing agents, phenoxyethanol and an aqueous based diluent.

In yet another embodiment, the hair straightening formulations provides a gelatinous aqueous thermal hair straightening and conditioning formulations that preferably impart a firm and silky look and feel to hair and inhibits wind and motion induced hair scattering during use. The formulations comprise glyoxal, amino acids of hair keratin, epigallocatechin gallate, water, propylene glycol, cetearyl alcohol, cetarimonium chloride, amondimethicone, cyclopentasiloxane, dimethicone and fragrance. The hair straightener and conditioner formulations preferably are used before hot iron straightening of curly hair, and imparts a smooth and silky feel to hair.

Also provided are uses of these hair formulations set forth above in straightening hair. Specifically, methods for straightening hair are provided comprising applying an amount of these formulations and for a time effective to straighten hair.

Further provided are one or more hair straightening systems comprising (a) the hair straightening formulations set forth above; (b) one or more shampoos and (c) one or more conditioners.

The term "modulates hair frizz" and "defrizzes hair" are used interchangeably. In a particular embodiment, at least one of the shampoos and/or at least one of the conditioners modulates hair frizz. As defined herein "modulates" means that it either reduces or prevents hair frizz. In another particular embodiment, the hair straightening system comprises at least one leave-in conditioner.

As defined herein, "leave-in" conditioner is a conditioner that is applied to the hair and is not removed by rinsing.

Further provided are one or more methods for straightening hair. In one or more methods, the hair straightening systems set forth above are used.

One or more of the methods comprise the following steps:
(a) washing said hair with shampoo to obtain washed hair;
(b) drying washed hair of step (a) to obtain dried hair;
(c) applying the hair straightening formulations set forth above to said dried hair of step (b) to obtain treated hair;
(d) drying the treated hair of step (c) to obtain dried hair;
(e) maintaining the dried hair in step (d) for an amount of time effective to obtain maintained dried hair;
(f) washing the maintained dried hair of step (e) with shampoo to obtain shampooed hair;
(g) treating shampooed hair of step (f) with conditioner for an amount of time effective to obtain conditioned hair;
(h) rinsing conditioned hair of step (g) with water to obtain rinsed hair and
(i) treating rinsed hair with conditioner to obtain straightened hair.

In particular embodiments, the shampoo used in step (f) is selected to modulate frizz of hair and/or the conditioner used in step (g) is selected to modulate frizz of hair. In another particular embodiment, the conditioner used in step (i) comprises a leave-in-conditioner.

DETAILED DESCRIPTION OF EMBODIMENTS

While the formulations, methods and systems heretofore are susceptible to various modifications and alternative forms, exemplary embodiments will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

In the present specification, the terms "solution", "preparation", "composition" and "formulation" can be used interchangeably.

Where a range of values is provided, it is understood that each intervening value, to the tenth of the unit of the lower limit unless the context clearly dictates otherwise, between the upper and lower limit of that range and any other stated or intervening value in that stated range, is included therein. Smaller ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the relevant art. Although any methods and materials similar or equivalent to those described herein can also be used, the preferred methods and materials are now described.

It must be noted that as used herein and in the appended claims, the singular forms "a," "and" and "the" include plural references unless the context clearly dictates otherwise.

The hair straightening formulations contain the following active ingredients: one or more keratin cross-linking agents and one or more keratin protein fractions. They may also comprise one or more surfactants, one or more emollients, one or more emulsifiers, one or more skin cleansing agents, one or more preservatives, and/or one or more aqueous based diluents. They may also contain one or more thickeners. Each of the components is described below.

Hair Straightening Formulations
Keratin Cross-Linking Agents

The preferable agent comprises a nonformaldehyde aldehyde, preferably a dialdehyde and even more preferably glyoxal.

It should be noted that although glyoxal is the preferred aldehyde in this embodiment, other aldehydes such as gluteraldehyde, adipaldehyde, benzaldehyde, acetaldehyde, methanal, butanal, propanal, cinnamaldehyde, etc., can be substituted for the fixative effect. In fact, since the effect is mediated by the Maillard Reaction and cross-linking of the keratin fibers, all other Maillard reactants and cross-linking agents can also be potentially substituted for glyoxal. This chemical cross-linking effect can involve sugars, such as dihydroxyacetone, acetones and ethers that undergo the Maillard reaction. Chemical compounds which are known to be useable as fixatives for cross-linking keratin (or collagen) besides the aldehydes, include hexamethylene diisocyanate and certain polyepoxy compounds, imidoesters, N-hydroxysuccinimide-esters, maleimides, haloacetyls, pyridyl disulfides, hydrazides, carbodiimides, and aryl azides. Representative epoxy-type reactants include epihalohydrins, e.g., epichlorohydrin and epibromohydrin with epichlorohydrin being the preferred epihalohydrin, diepoxides, e.g., 1,4-butanediol-diglycidyl ethers, and precursors of epihalohydrins and diepoxides, e.g., 1,3-dichloropropanol-2 and 1,4-dichloro-2,3-dihydroxybutane.

Polyepoxy compounds which have heretofore been known for use as collagen cross linking agents are described in U.S. Pat. Nos. 4,806,959 (Noishiki et al.) and 5,080,670 (Imamura et al.). At least some of these heretofore-known polyepoxy fixatives are commercially available under the trademark Denacol™ from Nagase Chemicals, Ltd., Osaka, Japan. In particular, one difunctional epoxy compound which has been disclosed for use as a collagen cross linking agent is an ethylene glycol diglycidyl ether based compound commercially available from Nagase Chemicals, Ltd. of Osaka, Japan under the designation Denacol Ex-810.

Other epoxy compounds which have been disclosed for use as collagen cross linking agents include those which are commercially available as Denacol Ex-313 and Dencacol Ex-314 from Nagase Chemicals, Ltd. of Osaka, Japan. Denacol Ex-313 and Ex-314 are specifically described in U.S. Pat. No. 5,080,670 (Imamura et al.). Denacol Ex-313 and Denacol Ex-314.

In general, cross-linking agents of low molecular weight cause relatively fast crosslinking of keratin while cross-linking agents of high molecular weight are relatively slow acting in this regard. Thus, at a given temperature and pressure, the cross-link density or number of cross-linkages formed may be affected by both time of exposure of the fixative (i.e., cross-linking agent) solution and the molecular weight (or molecular weight distribution) of the particular cross linking agent(s) being used. Additionally, the crosslink density or number of cross linkages formed in the keratin network may be affected by other factors including a) the concentration of the cross-linking agent in the fixative solution, b) the pH of the fixative solution, and c) any alteration or change in the physical conditions such as temperature and pressure.

The keratin cross-linking agent may be present in an amount of about 0.05%-10% by weight. In a preferred embodiment, the cross-linking agent is present in the amount of about 0.1-1% by weight.

Keratin Protein Fractions

The keratin protein fractions used in these formulations of comprise hydrolyzed keratin produced by alkaline and/or enzymatic hydrolysis using methods known in the art. The keratin hydrolysate is about 1,000-3,000 molecular weight. The keratin may be derived from human or other mammalian sources such as goat hair (U.S. Patent Appln. Pub. No. 20070048235), hoof or horn meals, (U.S. Pat. No. 6,555, 505). Alternatively, "keratin protein fraction" is a purified form of keratin that contains predominantly, although not entirely, one distinct protein group as described in U.S. Pat. No. 7,148,327. In a particular embodiment, the keratin protein fraction is intact intermediate filament protein capable of acting as a protective keratin layer. The keratin protein fraction may comprise a keratin hydrolysate and a purified form of keratin; keratin hydrolysate and one or more intact intermediate filament proteins capable of acting as a protective keratin layer or a mixture of intact intermediate filament proteins. The keratin protein fraction may be present in an amount of about 0.05% to about 15% by weight with a preferred range of about 0.5-5% by weight.

Surfactants

Another ingredient which may be included in these hair straightening formulations is one or more surfactants. Surfactants are surface-active agents that are able to reduce the surface tension of water and cause the product to slip across or onto the skin. Surfactants also include detergents and soap. In one embodiment, the surfactants are amphoteric. Anionic or cationic surfactants may be used as well. Surfactants that may be used comprise, or alternatively include but are not limited to, 3-aminopropane sulfonic acid, almond amide DEA, almond amidopropyl betaine, almond amidopropylamine oxide, aluminum hydrogenated tallow glutamate, aluminum lanolate, aminoethyl sulfate, aminopropyl lauryl glutamine, ammonium C12-15 alkyl sulfate, ammonium C12-15 pareth sulfate, ammonium C12-16 alkyl sulfate, ammonium C9-10 perfluoroalkylsulfonate, ammonium capryleth sulfate, ammonium capryleth-3 sulfate, ammonium cocomonoglyceride sulfate, ammonium coco-sulfate, ammonium cocoyl isethionate, ammonium cocoyl sarcosinate, ammonium cumene sulfonate, ammonium dimethicone copolyol sulfate, ammonium dodecylbenzenesulfonate, ammonium isostearate, ammonium laureth sulfate, ammonium laureth-12 sulfate, ammonium laureth-5 sulfate, ammonium laureth-6 carboxylate, ammonium laureth-7 sulfate, ammonium laureth-8 carboxylate, ammonium laureth-9 sulfate, ammonium lauroyl sarcosinate, ammonium lauryl sulfate, ammonium lauryl sulfosuccinate, ammonium myreth sulfate, ammonium myristyl sulfate, ammonium nonoxynol-30 sulfate, ammonium nonoxynol-4 sulfate, ammonium oleate, ammonium palm kernel sulfate, ammonium polyacrylate, ammonium stearate, ammonium tallate, ammonium xylene sulfonate, ammonium xylene sulfonate, amp-isostearoyl gelatin/keratin amino acids/lysine hydroxypropyltrimonium chloride, amp-isostearoyl hydrolyzed collagen, apricot kernel oil PEG-6 esters, apricot amide DEA, apricot amidopropyl betaine, arachideth-20, avocadamide DEA, avocadamidopropyl betaine, babassuamide DEA, babassuamidopropyl betaine, babassuamidopropylamine oxide, behenalkonium chloride, behenamide DEA, behenamide MEA, behenamidopropyl betaine, behenamine oxide, behentrimonium methosulfate, behenyl betaine, buteth-3 carboxylic acid, butyl polyglucose, C10-14 alkyl benzenesulfonic acid, C11-15 pareth-12, C11-15 pareth-20, C11-15 pareth-30, C11-15 pareth-40, C11-15 pareth-7 carboxylic acid, C11-15 pareth-9, C11-21-pareth-10, C12-13 pareth-10 phosphate, C12-13 pareth-5 carboxylic acid, C12-13 pareth-7, C12-15 pareth-11, C12-15 pareth-12, C12-15 pareth-2 phosphate, C12-15 pareth-7 carboxylic acid, C12-15 pareth-9, C12-15 pareth-9 hydrogenated tallowate, C14-15 pareth-13, C14-15 pareth-8 carboxylic acid, C22-24 pareth-33, calcium laurate, calcium myristate, canolamidopropyl betaine, caprylyl/capryl glucoside, caprylyl pyrrolidone, carboxymethyl isostearamidopropyl morpholine, cellulose acetate propionate carboxylate, ceteareth-100, ceteareth-15, ceteareth-17, ceteareth-2 phosphate, ceteareth-20, ceteareth-25, ceteareth-25 carboxylic acid, ceteareth-27, ceteareth-30, ceteareth-4 phosphate, ceteareth-40, ceteareth-5 phosphate, ceteareth-50, ceteareth-55, ceteareth-80, cetearyl polyglucose, ceteth-12, ceteth-14, ceteth-15, ceteth-16, ceteth-20, ceteth-24, ceteth-25, ceteth-45, cetethyl morpholinium ethosulfate, cetethyldimonium bromide, cetoleth-15, cetoleth-24, cetoleth-25, cetoleth-6, cetrimonium tosylate, cetyl betaine, cetyl PPG-2 isodeceth-7 carboxylate, cetylpyridinium chloride, cholesteryl/behenyl/octyldodecyl lauroyl glutamate, cocamide, cocamide DEA, cocamide MEA, cocamide MIPA, cocamidoethyl betaine, cocamidopropyl betaine, cocamidopropyl dimethylamine, cocamidopropyl dimethylamine dihydroxymethylpropionate, cocamidopropyl dimethylamine hydrolyzed collagen, cocamidopropyl dimethylamine lactate, cocamidopropyl dimethylamine propionate, cocamidopropyl dimethylaminohydroxypropyl hydrolyzed collagen, cocamidopropyl dimethylammonium C8-16 isoalkylsuccinyl lactoglobulin sulfonate, cocamidopropyl hydroxysultaine, cocamidopropyl lauryl ether, cocamidopropylamine oxide, cocamidopropyldimonium hydroxypropyl hydrolyzed collagen, cocamine oxide, cocaminobutyric acid, cocaminopropionic acid, coceth-4 polyglucose, coceth-7 carboxylic acid, coco/oleamidopropyl betaine, cocoamphodipropionic acid, cocobetainamido amphopropionate, coco-betaine, cocodimonium hydroxypropyl silk amino acids, coco-ethyldimonium ethosulfate, coco-glucoside, coco-hydroxysultaine, coco-morpholine oxide, coconut acid, coco-polyglucose, coco-sultaine, cocotrimonium chloride, cocoyl benzyl hydroxyethyl imidazolinium chloride, cocoyl hydrolyzed collagen, cocoyl hydroxyethyl imidazoline, cocoyl sarcosinamide DEA, cocoyl sarcosine, corn acid, cyclopentane carboxylic acid, DEA-C12-15 alkyl sulfate, DEA-cetyl phosphate, DEA-cetyl sulfate, DEA-cocoamphodipropionate, DEA-cyclocarboxypropyloleate, DEA-dodecylbenzenesulfonate, DEA-isostearate, DEA-laureth sulfate, DEA-lauryl sulfate, DEA-methyl myristate sulfonate, DEA-myreth sulfate, DEA-myristate, DEA-myristyl sulfate, DEA-oleth-10 phosphate, DEA-oleth-20 phosphate, DEA-oleth-3 phosphate, DEA-oleth-5 phosphate, deceth-4 phosphate, deceth-7 carboxylic acid, decyl betaine, decyl glucoside, decyl polyglucose, decylamine oxide, diammonium dimethicone copolyol sulfosuccinate, diammonium lauramido-MEA sulfosuccinate, diammonium lauryl sulfosuccinate, diammonium oleamido PEG-2 sulfosuccinate, diamyl sodium sulfosuccinate, dicapryl sodium sulfosuccinate, dicetyldimonium chloride, dicocodimonium chloride, dicyclohexyl sodium sulfosuccinate, didecyldimonium chloride, diethanolaminooleamide DEA, diethylamine laureth sulfate, diethylaminoethyl cocoate, diethylaminoethyl PEG-5 cocoate, diethylaminoethyl stearate, diheptyl sodium sulfosuccinate, dihexyl sodium sulfosuccinate, dihydrogenated C16-18 amido benzoic acid, dihydrogenated tallow benzylmonium chloride, dihydrogenated tallow methylamine, dihydrogenated tallow phthalate, dihydroxyethyl C12-15 alkoxypropylamine oxide, dihydroxyethyl C8-10 alkoxypropylamine oxide, dihydroxyethyl C9-11 alkoxypropylamine oxide, dihydroxyethyl cocamine oxide, dihydroxyethyl lauramine oxide, dihydroxyethyl soya glycinate, dihydroxyethyl stearamine oxide, dihydroxyethyl tallow glycinate, dihydroxyethyl tallowamine HCl, dihydroxyethyl tallowamine oleate, dihydroxyethyl tallowamine oxide, diisobutyl sodium sulfosuccinate, dilaureth-10 phosphate, dilaureth-4 dimonium chloride, dilauryldimonium chloride, dilinoleamidopropyl dimethylamine dimethicone copolyol phosphate, dimethicone propyl PG-betaine, dimethyl cocamine, dinonoxynol-9 citrate, dioctyl sodium sulfosuccinate, dioctyldodeceth-2 lauroyl glutamate, dioctyldodecyl lauroyl glutamate, dioleth-8 phosphate, dipropylene glycol salicylate, disodium bisethylphenyl triaminotriazine stilbenedisulfonate, disodium C12-15 pareth sulfosuccinate, disodium caproamphodiacetate, disodium caproamphodipropionate, disodium capryloamphodiacetate, disodium capryloamphodipropionate, disodium cetearyl sulfosuccinate, disodium cocamido MEA-sulfosuccinate, disodium cocamido MIPA-sulfosuccinate, disodium cocamido PEG-3 sulfosuccinate, disodium cocaminopropyl iminodiacetate, disodium cocoamphocarboxyethylhydroxypropylsulfonate, disodium cocoamphodiacetate, disodium cocoamphodipropionate, disodium cocopolyglucose citrate, disodium cocopolyglucose sulfosuccinate, disodium cocoyl butyl gluceth-10 sulfosuccinate, disodium cocoyl glutamate, disodium deceth-5 sulfosuccinate, disodium deceth-6 sulfosuccinate, disodium dicarboxyethyl cocopropylenediamine, disodium dihydroxyethyl sulfosuccinylundecylenate, disodium dimethicone copolyol sulfosuccinate, disodium distyrylbiphenyl disulfonate, disodium hydrogenated cottonseed glyceride sulfosuccinate, disodium hydrogenated tallow glutamate, disodium hydroxydecyl sorbitol citrate, disodium isodecyl sulfosuccinate, disodium isostearamido MEA-sulfosuccinate, disodium isostearamido MIPA-sulfosuccinate, disodium isostearoamphodiacetate, disodium isostearoamphodipropionate, disodium isostearyl sulfosuccinate, disodium laneth-5 sulfosuccinate, disodium lauramido MEA-sulfosuccinate, disodium lauramido PEG-2 sulfosuccinate, disodium lauramido PEG-5 sulfosuccinate, disodium laureth sulfosuccinate, disodium laureth-12 sulfosuccinate, disodium laureth-5 carboxyamphodiacetate, disodium laureth-6 sulfosuccinate, disodium laureth-7 citrate, disodium laureth-9 sulfosuccinate, disodium lauriminodipropionate, disodium lauroamphodiacetate, disodium lauroamphodipropionate, disodium lauryl sulfosuccinate, disodium myristamido MEA-sulfosuccinate, disodium nonoxynol-10 sulfosuccinate, disodium oleamido MEA-sulfosuccinate, disodium oleamido MIPA-sulfosuccinate, disodium oleamido PEG-2 sulfosuccinate, disodium oleoamphodipropionate, disodium oleth-3 sulfosuccinate, disodium oleyl sulfosuccinate, disodium palmitamido PEG-2 sulfosuccinate, disodium palmitoleamido PEG-2 sulfosuccinate, disodium PEG-10 laurylcitrate sulfosuccinate, disodium PEG-4 cocamido MIPA-sulfosuccinate, disodium PEG-8 glyceryl caprylate/caprate, disodium PEG-8 ricinosuccinate, disodium PPG-2-isodeceth-7 carboxyamphodiacetate, disodium ricinoleamido MEA-sulfosuccinate, disodium sitostereth-14 sulfosuccinate, disodium stearamido MEA-sulfosuccinate, disodium steariminodipropionate, disodium stearoamphodiacetate, disodium stearyl sulfosuccinamate, disodium stearyl sulfosuccinate, disodium succinate, disodium succinoyl glycyrrhetinate, disodium tallamido MEA-sulfosuccinate, disodium tallow sulfosuccinamate, disodium tallow amido MEA-sulfosuccinate, disodium tallow amphodiacetate, disodium tallow iminodipropionate, disodium tetrapropenyl succinate, disodium tridecylsulfosuccinate, disodium undecylenamido MEA-sulfosuccinate, disodium undecylenamido PEG-2 sulfosuccinate, disodium wheat germamido MEA-sulfosuccinate, disodium wheat germamido PEG-2 sulfosuccinate, disodium wheat germ amphodiacetate, disoyadimonium chloride, distearteh-2 lauroyl glutamate, disteareth-5 lauroyl glutamate, disteareth-6 dimonium chloride, ditallowamidoethyl hydroxypropylamine, ditallowedimonium chloride, di-TEA-oleamido PEG-2 sulfosuccinate, di-TEA-palmitoyl aspartate, ditridecyl sodium sulfosuccinate, dodecylbenzene sulfonic acid, dodecylbenzyltrimonium chloride, dodecylxylylditrimonium chloride, dodoxynol-12, dodoxynol-5, dodoxynol-6, dodoxynol-7, dodoxynol-9, erucamidopropyl hydroxysultaine, ethyl butylacetylaminopropionate, ethyl guiazulene sulfonate, ethyl PEG-15 cocamine sulfate, glycol stearate, hexeth-4 carboxylic acid, hydrogenated castor oil, hydrogenated coconut acid, hydrogenated ditallowamine, hydrogenated menhaden acid, hydrogenated tallow amide, hydrogenated tallow betaine, hydrogenated tallowamide DEA, hydrogenated tallowamine, hydrogenated tallowamine oxide, hydrogenated tallowtrimonium chloride, hydrolyzed beeswax, hydroxyceteth-60, hydroxyethyl carboxymethyl cocamidopropylamine, hydroxyethyl cetyldimonium chloride, hydroxyethyl cetyldimonium phosphate, hydroxyethyl hydroxypropyl C12-15 alkoxypropylamine oxide, hydroxyethylbutylamine laureth sulfate, isoceteth-30, isopropanolamine lanolate, isopropyl hydroxycetyl ether, isopropylamine dodecylbenzenesulfonate, isostearamidomorpholine stearate, isostearamidopropyl betaine, isostearamidopropyl morpholine oxide, isostearamidopropylamine oxide, isosteareth-11 carboxylic acid, isosteareth-50, isosteareth-6 carboxylic acid, isostearic acid, isostearoyl hydrolyzed collagen, laneth-40, laneth-50, laneth-75, lanolinamide DEA, lauramide/myristamide DEA, lauramidopropyl betaine, lauramidopropylamine oxide, lauramine oxide, laureth-1, laureth-10, laureth-10 carboxylic acid, laureth-11 carboxylic acid, laureth-13 carboxylic acid, laureth-14 carboxylic acid, laureth-17 carboxylic acid, laureth-2, laureth-20, laureth-23, laureth-25, laureth-3, laureth-3 carboxylic acid, laureth-3 phosphate, laureth-30, laureth-4, laureth-4 carboxylic acid, laureth-40, laureth-5, laureth-5 carboxylic acid, laureth-6, laureth-6 carboxylic acid, laureth-6 citrate, laureth-7, laureth-7 citrate, laureth-7 tartrate, laureth-8 phosphate, lauroamphodipropionic acid, lauroyl hydrolyzed collagen, lauroyl sarcosine, lauryl betaine, lauryl hydroxysultaine, lauryl isoquinolinium bromide, lauryl polyglucose, lauryl pyrrolidone, lauryl sultaine, laurylpyridinium chloride, lysine thiazolidine carboxylate, magnesium cocoate, magnesium coco-sulfate, magnesium lanolate, magnesium laureth sulfate, magnesium laureth-11 carboxylate, magnesium laureth-16 sulfate, magnesium laureth-5 sulfate, magnesium laureth-8 sulfate, magnesium lauryl hydroxypropyl sulfonate, magnesium lauryl sulfate, magnesium myreth sulfate, magnesium oleth sulfate, magnesium PEG-3 cocamide sulfate, magnesium tallowate, mannitan oleate, MEA-dicetearyl phosphate, MEA-laureth sulfate, MEA-laureth-6 carboxylate, MEA-lauryl sulfate, MEA-PPG-6-laureth-7-carboxylate, meroxapol 105, meroxapol 108, meroxapol 171, meroxapol 172, meroxapol 174, meroxapol 178, meroxapol 251, meroxapol 252, meroxapol 254, meroxapol 255, meroxapol 258, meroxapol 311, meroxapol 312, meroxapol 314, methoxy-PEG-7 rutinyl succinate, methyl morpholine oxide, methylpyrrolidone, methylbenzethonium chloride, minkamide DEA, minkamidopropyl betaine, minkamidopropyl dimethylamine, minkamidopropylamine oxide, MIPA C12-15 pareth sulfate, MIPA-dodecylbenzenesulfonate, MIPA-laureth sulfate, MIPA-lauryl sulfate, mixed isopropanolamines lanolate, mixed isopropanolamines lauryl sulfate, mixed isopropanolamines myristate, myreth-2 myristate, myreth-3 carboxylic acid, myreth-3 myristate, myreth-5 carboxylic acid, myristamidopropyl betaine, myristamidopropyl dimethylamine dimethicone copolyol phosphate, myristamidopropyl dimethylamine phosphate, myristamidopropylamine oxide, myristamine oxide, myristaminopropionic acid, myristoyl hydrolyzed collagen, myristoyl sarcosine, myristyl/cetyl amine oxide, myristyl betaine, noneth-8, nonoxynol-10 carboxylic acid, nonoxynol-10 phosphate, nonoxynol-100, nonoxynol-11, nonoxynol-12, nonoxynol-13, nonoxynol-14, nonoxynol-15, nonoxynol-18, nonoxynol-2, nonoxynol-20, nonoxynol-23, nonoxynol-30, nonoxynol-4, nonoxynol-40, nonoxynol-44, nonoxynol-5, nonoxynol-5 carboxylic acid, nonoxynol-50, nonoxynol-6, nonoxynol-6 phosphate, nonoxynol-7, nonoxynol-8, nonoxynol-8 carboxylic acid, nonoxynol-9, nonoxynol-9 phosphate, nonyl nonoxynol-10, nonyl nonoxynol-10 phosphate, nonyl nonoxynol-100, nonyl nonoxynol-15 phosphate, nonyl nonoxynol-150, nonyl nonoxynol-24 phosphate, nonyl nonoxynol-49, nonyl nonoxynol-7 phosphate, nonyl nonoxynol-9 phosphate, octeth-3 carboxylic acid, octoxynol-1, octoxynol-10, octoxynol-11, octoxynol-13, octoxynol-16, octoxynol-20 carboxylic acid, octoxynol-3, octoxynol-30, octoxynol-40, octoxynol-5, octoxynol-7, octoxynol-70, octoxynol-8, octoxynol-9, octoxynol-9 carboxylic acid, oleamidopropyl betaine, oleamidopropyl hydroxysultaine, oleamidopropylamine oxide, oleamine oxide, oleoyl hydrolyzed collagen, oleoyl sarcosine, oleth-10, oleth-10 carboxylic acid, oleth-10 phosphate, oleth-12, oleth-15, oleth-16, oleth-2, oleth-20, oleth-20 phosphate, oleth-23, oleth-25, oleth-3 carboxylic acid, oleth-3 phosphate, oleth-4 phosphate, oleth-44, oleth-5 phosphate, oleth-50, oleth-6 carboxylic acid, oleyl betaine, olivamide DEA, olivamidopropyl betaine, olivamidopropylamine oxide, olive oil PEG-10 esters, palm kernelamide DEA, palm kernelamide MEA, palm kernelamide MIPA, palm kernelamidopropyl betaine, palmamide DEA, palmamide MEA, palmamide MIPA, palmamidopropyl betaine, palmitamidopropyl betaine, palmitamidopropylamine oxide, palmitamine oxide, palmitoyl hydrolyzed collagen, palmitoyl hydrolyzed wheat protein, pca ethyl cocoyl arginate, peanutamide MEA, peanutamide MIPA, PEG/PPG-300/55 copolymer, PEG-10 castor oil, PEG-10 cocamine, PEG-10 coco-benzonium chloride, PEG-10 isostearate, PEG-10 soyamine, PEG-10 stearate, PEG-10 stearyl benzonium chloride, PEG-100 castor oil, PEG-100 hydrogenated castor oil, PEG-100 lanolin, PEG-100 stearate, PEG-11 cocamide, PEG-120 glyceryl stearate, PEG-120 stearate, PEG-15 castor oil, PEG-15 cocamine, PEG-15 cocomonium chloride, PEG-15 hydrogenated tallow amine, PEG-15 oleammonium chloride, PEG-15 soyamine, PEG-15 stearmonium chloride, PEG-150 distearate, PEG-150 laurate, PEG-150 oleate, PEG-150 stearate, PEG-16 hydrogenated castor oil, PEG-175 distearate, PEG-2 castor oil, PEG-2 coco-benzonium chloride, PEG-2 cocomonium chloride, PEG-2 hydrogenated tallow amine, PEG-2 oleammonium chloride, PEG-2 sorbitan isostearate, PEG-2 soyamine, PEG-2 stearamide carboxylic acid, PEG-20 castor oil, PEG-20 cocamine, PEG-20 glyceryl isostearate, PEG-20 hydrogenated castor oil, PEG-20 hydrogenated tallow amine, PEG-20 laurate, PEG-20 myristate, PEG-20 oleate, PEG-20 palmitate, PEG-20 sorbitan beeswax, PEG-20 sorbitan isostearate, PEG-20 stearate, PEG-20 tallate, PEG-200 castor oil, PEG-200 glyceryl stearate, PEG-200 glyceryl tallowate, PEG-200 hydrogenated castor oil, PEG-200 trihydroxystearin, PEG-23 oleate, PEG-25 castor oil, PEG-25 diethylmonium chloride, PEG-25 glyceryl stearate, PEG-25 hydrogenated castor oil, PEG-28 glyceryl tallowate, PEG-29 castor oil, PEG-3 castor oil, PEG-3 cocamide, PEG-3 lauramine oxide, PEG-3 oleamide, PEG-30 castor oil, PEG-30 glyceryl cocoate, PEG-30 glyceryl isostearate, PEG-30 glyceryl oleate, PEG-30 glyceryl stearate, PEG-30 hydrogenated castor oil, PEG-30 hydrogenated tallow amine, PEG-30 oleamine, PEG-30 stearate, PEG-32 laurate, PEG-32 oleate, PEG-32 stearate, PEG-33 castor oil, PEG-35 castor oil, PEG-35 hydrogenated castor oil, PEG-35 stearate, PEG-36 castor oil, PEG-36 oleate, PEG-36 stearate, PEG-4 castor oil, PEG-4 laurate, PEG-4 stearamide, PEG-40 castor oil, PEG-40 hydrogenated castor oil, PEG-40 hydrogenated tallow amine, PEG-40 sorbitan diisostearate, PEG-40 sorbitan perisostearate, PEG-40 sorbitan peroleate, PEG-40 sorbitan stearate, PEG-40 sorbitol hexaoleate, PEG-40 stearate, PEG-44 sorbitan laurate, PEG-45 hydrogenated castor oil, PEG-45 stearate, PEG-45 stearate phosphate, PEG-4-PPG-7 C13/C15 alcohol, PEG-5 castor oil, PEG-5 cocamide, PEG-5 ditridecylmonium chloride, PEG-5 glyceryl stearate, PEG-5 hydrogenated castor oil, PEG-5 hydrogenated corn glycerides, PEG-5 soyamine, PEG-5 stearate, PEG-5 stearyl ammonium chloride, PEG-5 stearyl ammonium lactate, PEG-5 tallow benzonium chloride, PEG-50 castor oil, PEG-50 hydrogenated castor oil, PEG-50 stearamine, PEG-50 stearate, PEG-6 cocamide, PEG-6 oleate, PEG-6 palmitate, PEG-6 sorbitan beeswax, PEG-60 castor oil, PEG-60 glyceryl isostearate, PEG-60 hydrogenated castor oil, PEG-60 sorbitan stearate, PEG-66 trihydroxystearin, PEG-7 cocamide, PEG-7 glyceryl cocoate, PEG-7 hydrogenated castor oil, PEG-7 oleate, PEG-75 castor oil, PEG-75 dioleate, PEG-75 lanolin, PEG-75 lanolin oil, PEG-75 lanolin wax, PEG-75 laurate, PEG-75 oleate, PEG-75 sorbitan laurate, PEG-75 stearate, PEG-78 glyceryl cocoate, PEG-8 castor oil, PEG-8 laurate, PEG-8 propylene glycol cocoate, PEG-8 ricinoleate, PEG-8 sorbitan beeswax, PEG-8 soyamine, PEG-8 stearate, PEG-80 glyceryl cocoate, PEG-80 hydrogenated castor oil, PEG-80 jojoba acid, PEG-80 jojoba alcohol, PEG-80 sorbitan laurate, PEG-80 sorbitan palmitate, PEG-85 lanolin, PEG-9 castor oil, PEG-9 ricinoleate, PEG-90 stearate, pentaerythrityl tetraisostearate, poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, poloxamer 407, polyglyceryl-4-PEG-2 cocamide, polysorbate 20, polysorbate 40, polysorbate 60, polysorbate 65, polysorbate 80, polysorbate 85, potassium abietoyl hydrolyzed collagen, potassium C9-15 alkyl phosphate, potassium castorate, potassium cetyl phosphate, potassium cocoate, potassium cocoyl glutamate, potassium cocoyl hydrolyzed collagen, potassium cornate, potassium cyclocarboxypropyloleate, potassium dihydroxyethyl cocamine oxide phosphate, potassium dodecylbenzenesulfonate, potassium laurate, potassium lauroyl collagen amino acids, potassium lauroyl hydrolyzed collagen, potassium lauroyl hydrolyzed soy protein, potassium lauryl hydroxypropyl sulfonate, potassium lauryl sulfate, potassium methyl cocoyl taurate, potassium myristate, potassium myristoyl hydrolyzed collagen, potassium octoxynol-12 phosphate, potassium oleate, potassium oleoyl hydrolyzed collagen, potassium olivate, potassium palmitate, potassium ricinoleate, potassium stearate, potassium stearoyl hydrolyzed collagen, potassium tallowate, potassium toluenesulfonate, potassium undecylenoyl hydrolyzed collagen, potassium xylene sulfonate, PPG-10 cetyl ether, PPG-10 cetyl ether phosphate, PPG-15-PEG-11 hydrogenated lauryl alcohol ether, PPG-17 butyl ether, PPG-20 butyl ether, PPG-24 butyl ether, PPG-25 diethylmonium chloride, PPG-3 hydrogenated castor oil, PPG-30-buteth-30, PPG-4 laureth-5, PPG-40 diethylmonium chloride, PPG-50 cetyl ether, PPG-5-ceteth-10 phosphate, PPG-5-ceteth-20, PPG-8-ceteth-10, PPG-8-ceteth-20, PPG-9 diethylmonium chloride, propylene glycol soyate, quaternium-14, quaternium-18, quaternium-24, quaternium-52, raffinose oleate, rapeseedamidopropyl benzyldimonium chloride, ricinoleamidopropyl betaine, ricinoleth-40, saponins, sesamide DEA, sesamidopropyl betaine, sesamidopropyl dimethylamine, sesamidopropylamine oxide, sodium/MEA laureth-2 sulfosuccinate, sodium/TEA-lauroyl collagen amino acids, sodium/TEA-lauroyl hydrolyzed collagen, sodium/TEA-lauroyl hydrolyzed keratin, sodium/TEA-lauroyl keratin amino acids, sodium/TEA-undecylenoyl collagen amino acids, sodium/TEA-undecylenoyl hydrolyzed collagen, sodium behenoyl lactylate, sodium bisglycol ricinosulfosuccinate, sodium butoxynol-12 sulfate, sodium C11-15 pareth-7 carboxylate, sodium C12-13 pareth sulfate, sodium C12-14 olefin sulfonate, sodium C12-15 alkoxypropyl iminodipropionate, sodium C12-15 alkyl sulfate, sodium C12-15 pareth sulfate, sodium C12-15 pareth-15 sulfonate, sodium C12-15 pareth-3 sulfonate, sodium C12-15 pareth-6 carboxylate, sodium C12-15 pareth-7 carboxylate, sodium C12-15 pareth-7 sulfonate, sodium C12-18 alkyl sulfate, sodium C13-17 alkane sulfonate, sodium C14-16 olefin sulfonate, sodium C14-17 alkyl sec sulfonate, sodium C14-18 olefin sulfonate, sodium C16-18 olefin sulfonate, sodium C16-20 alkyl sulfate, sodium C8-16 isoalkylsuccinyl lactoglobulin sulfonate, sodium C9-22 alkyl sec sulfonate, sodium caproamphoacetate, sodium caproamphohydroxypropylsulfonate, sodium caproamphopropionate, sodium caprylate, sodium capryleth-2 carboxylate, sodium capryleth-9 carboxylate, sodium capryloamphoacetate, sodium capryloamphohydroxypropylsulfonate, sodium capryloamphopropionate, sodium caprylyl sulfonate, sodium carboxyethyl tallow polypropylamine, sodium carboxymethyl cocopolypropylamine, sodium carboxymethyl oleyl polypropylamine, sodium carboxymethyl tallow polypropylamine, sodium castorate, sodium cetearyl sulfate, sodium ceteth-13 carboxylate, sodium cetyl sulfate, sodium cocaminopropionate, sodium coceth sulfate, sodium coco/hydrogenated tallow sulfate, sodium cocoamphoacetate, sodium cocoamphohydroxypropylsulfonate, sodium cocoamphopropionate, sodium cocoate, sodium cocoglyceryl ether sulfonate, sodium cocomonoglyceride sulfate, sodium cocomonoglyceride sulfonate, sodium cocopolyglucose tartrate, sodium coco-sulfate, sodium cocoyl collagen amino acids, sodium cocoyl glutamate, sodium cocoyl hydrolyzed collagen, sodium cocoyl hydrolyzed keratin, sodium cocoyl hydrolyzed rice protein, sodium cocoyl hydrolyzed soy protein, sodium cocoyl hydrolyzed wheat protein, sodium cocoyl isethionate, sodium cocoyl lactylate, sodium cocoyl sarcosinate, sodium comamphopropionate, sodium cumenesulfonate, sodium cyclopentane carboxylate, sodium deceth sulfate, sodium deceth-2 carboxylate, sodium decylbenzenesulfonate, sodium dicarboxyethylcoco phosphoethyl imidazoline, sodium diethylaminopropyl cocoaspartamide, sodium dihydroxycetyl phosphate, sodium dilaureth-7 citrate, sodium dodecylbenzenesulfonate, sodium ethyl 2-sulfolaurate, sodium glycereth-1 polyphosphate, sodium glyceryl oleate phosphate, sodium guiazulene sulfonate, sodium hydrogenated tallow glutamate, sodium isostearoamphoacetate, sodium isostearoamphopropionate, sodium laneth sulfate, sodium lauramido diacetate, sodium lauramidopropyl hydroxyphostaine, sodium lauraminopropionate, sodium laurate, sodium laureth sulfate, sodium laureth-11 carboxylate, sodium laureth-12 sulfate, sodium laureth-13 carboxylate, sodium laureth-14 carboxylate, sodium laureth-17 carboxylate, sodium laureth-4 carboxylate, sodium laureth-4 phosphate, sodium laureth-5 carboxylate, sodium laureth-5 sulfate, sodium laureth-6 carboxylate, sodium laureth-7 sulfate, sodium laureth-7 tartrate, sodium laureth-8 sulfate, sodium lauriminodipropionate, sodium lauroampho PG-acetate phosphate, sodium lauroamphoacetate, sodium lauroamphohydroxypropylsulfonate, sodium lauroyl aspartate, sodium lauroyl glutamate, sodium lauroyl hydrolyzed collagen, sodium lauroyl isethionate, sodium lauroyl methylaminopropionate, sodium lauroyl sarcosinate, sodium lauroyl taurate, sodium lauryl phosphate, sodium lauryl sulfate, sodium lauryl sulfoacetate, sodium lignosulfonate, sodium methyl 2-sulfolaurate, sodium methyl cocoyl taurate, sodium methyl lauroyl taurate, sodium methyl myristoyl taurate, sodium methyl oleoyl taurate, sodium methyl palmitoyl taurate, sodium methyl stearoyl taurate, sodium methylnaphthalenesulfonate, sodium myreth sulfate, sodium myristate, sodium myristoamphoacetate, sodium myristoyl glutamate, sodium myristoyl isethionate, sodium myristoyl sarcosinate, sodium myristyl sulfate, sodium nonoxynol-1 sulfate, sodium nonoxynol-10 sulfate, sodium nonoxynol-4 sulfate, sodium nonoxynol-6 phosphate, sodium nonoxynol-9 phosphate, sodium octoxynol-2 ethane sulfonate, sodium octyl sulfate, sodium oleate, sodium oleoamphoacetate, sodium oleoamphohydroxypropylsulfonate, sodium oleoamphopropionate, sodium oleoyl isethionate, sodium oleth-7 phosphate, sodium oleth-8 phosphate, sodium olivate, sodium palm kernelate, sodium palmate, sodium palmitate, sodium PEG-6 cocamide carboxylate, sodium polydimethylglycinophenolsulfonate, sodium polynaphthalenesulfonate, sodium polystyrene sulfonate, sodium ricinoleoamphoacetate, sodium shale oil sulfonate, sodium soya hydrolyzed collagen, sodium stearate, sodium stearoamphoacetate, sodium stearoamphopropionate, sodium stearyl betaine, sodium stearyl sulfate, sodium tallamphopropionate, sodium tallow sulfate, sodium tallowamphoacetate, sodium tallowate, sodium toluenesulfonate, sodium trideceth sulfate, sodium trideceth-12 carboxylate, sodium trideceth-3 carboxylate, sodium trideceth-6 carboxylate, sodium trideceth-7 carboxylate, sodium trideceth-8 carboxylate, sodium tridecyl sulfate, sodium tridecylbenzenesulfonate, sodium trilaureth-4 phosphate, sodium undecylenoamphoacetate, sodium undecylenoamphopropionate, sodium wheat germamphoacetate, sodium xylenesulfonate, soya hydroxyethyl imidazoline, soyamide DEA, soyamidopropyl betaine, soyamidopropyl dimethylamine, soyamidopropyl ethyldimonium ethosulfate, soytrimonium chloride, stearamidopropyl betaine, stearamidopropyl dimethylamine, stearamidopropylamine oxide, stearamine oxide, steareth-10, steareth-100, steareth-2, steareth-20, steareth-21, steareth-25, steareth-27, steareth-30, steareth-40, steareth-50, stearoyl sarcosine, stearyl betaine, sucrose laurate, sucrose palmitate, sulfated castor oil, sulfated glyceryl oleate, sulfated olive oil, sulfated peanut oil, sulfonated castor oil, tallow amide, tallow amine, tallow betaine, tallow dihydroxyethyl betaine, tallow hydroxyethyl imidazoline, tallowalkonium chloride, tallowamidopropyl betaine, tallowamidopropyl dimethylamine, tallowamidopropyl hydroxysultaine, tallowamidopropylamine oxide, tallowamine oxide, tallowedimonium propyltrimonium dichloride, tallowtrimonium chloride, TEA-abietoyl hydrolyzed collagen, TEA-C 10-12 alkyl sulfate, TEA-C 10-14 alkyl benzenesulfonate, TEA-C 10-15 alkyl sulfate, TEA-C12-15 alkyl sulfate, TEA-cocoate, TEA-coco-sulfate, TEA-cocoyl glutamate, TEA-cocoyl hydrolyzed collagen, TEA-cocoyl sarcosinate, TEA-dodecylbenzenesulfonate, TEA-hydrogenated tallow glutamate, TEA-isostearate, TEA-isostearoyl hydrolyzed collagen, TEA-lauraminopropionate, TEA-laureth sulfate, TEA-lauroyl collagen amino acids, TEA-lauroyl glutamate, TEA-lauroyl hydrolyzed collagen, TEA-lauroyl keratin amino acids, TEA-lauroyl lactylate, TEA-lauroyl sarcosinate, TEA-lauryl sulfate, TEA-myristaminopropionate, TEA-myristate, TEA-myristoyl hydrolyzed collagen, TEAoleate, TEA-oleoyl hydrolyzed collagen, TEA-oleoyl sarcosinate, TEA-oleyl sulfate, TEA-palm kernel sarcosinate, TEA-palmitate, TEA-PEG-3 cocamide sulfate, TEA-stearate, TEA-tallate, TEA-tridecylbenzenesulfonate, TEA-undecylenoyl hydrolyzed collagen, tetrasodium dicarboxyethyl stearyl sulfosuccinamate, TIPA-laureth sulfate, TIPA-lauryl sulfate, TIPA-stearate, tocophereth-10, tocophereth-12, tocophereth-18, tocophereth-5, tocophereth-50, toluene sulfonic acid, triceteareth-4 phosphate, triceteth-5 phosphate, trideceth-12, trideceth-15 carboxylic acid, trideceth-19 carboxylic acid, trideceth-3 carboxylic acid, trideceth-4 carboxylic acid, trideceth-6, trideceth-6 phosphate, trideceth-7 carboxylic acid, trideceth-8, tridecylbenzenesulfonic acid, triheptanoin, trilauryl phosphate, triolein PEG-6 esters, trisodium lauroampho PG-acetate phosphate chloride, tristearyl phosphate, undecyl polyglucose, undecylenamidopropyl betaine, undecylenamidopropylamine oxide, undecylenoyl wheat amino acids, wheat germamide DEA, wheat germamidopropyl betaine, wheat germamidopropyl dimethylamine, wheat germamidopropyl dimethylamine lactate, wheat germamidopropylamine oxide, xylene sulfonic acid, zinc pentadecene tricarboxylate.

Surfactants in a particular embodiment comprise a polyoxyether of lauryl alcohol and/or ceteareth-20.

The surfactants may be present in an amount of about 0.1%-15% by weight with a preferred range of about 1%-10% by weight.

Emollients

A further ingredient of the hair straightening formulations are one or more emollients. As defined herein, an "emollient" is a material that protects against wetness or irritation, softens, soothes, supples, coats, lubricates, moisturizes, protects and/or cleanses the skin. Emollients used comprise one or more of: a silicone compound (e.g., dimethicone, cyclomethicone, dimethicone copolyol or a mixture of cyclopentasiloxane and dimethicone/vinyldimethicone cross polymer, cyclopentasiloxane polysilicone), polyols such as sorbitol, glycerin, propylene glycol, ethylene glycol, polyethylene glycol, caprylyl glycol, polypropylene glycol, 1,3-butane diol, hexylene glycol, isoprene glycol, xylitol; ethylhexyl palmitate; a triglyceride such as caprylic/capric triglyceride and fatty acid ester such as cetearyl isononanoate or cetyl palmitate. In a specific embodiment, the emollient is dimethicone, amidodimethicone, dimethiconol, cyclopentasiloxane, potassium dimethicone PEG-7 panthenyl phosphate, cetearyl isononanoate and/or cetyl palmitate.

The emollient generally comprises from about 0.5-15% and preferably about 1-10% by weight of the hair straightening formulations.

Emulsifiers

The formulations may also comprise one or more emulsifiers. Emulsifiers used in these hair straightening formulations comprise a copolymer of an unsaturated ester and styrene sulphonate monomer, cetearyl alcohol, glyceryl ester, polyoxyethylene glycol ether of cetearyl alcohol, stearic acid, polysorbate-20, ceteareth-20, lecithin, glycol stearate, polysorbate-60 and/or polysorbate-80. The emulsifier(s) generally comprises from about 0.05-15% by weight and preferably from about 0.1-10% by weight of the hair straightening formulations.

Preservatives

One or more preservatives may be included in the hair straightening formulations. Examples of such preservatives comprise one or more glycerin containing compound (e.g., glycerin or ethylhexylglycerin or phenoxyethanol), benzyl alcohol, EDTA, potassium sorbate and/or grapefruit seed extract. The preservative(s) generally comprises from about 0.1-5% by weight and preferably from about 0.3-3% by weight of the hair straightening formulations. In a preferred embodiment, the hair straightening formulations are paraben free. The preservative(s) generally comprises from 0.05-15% by weight and preferably from about 0.1-10% by weight of the hair straightening formulations.

Skin Protecting Agents

The hair straightening formulations comprise one or more skin protecting agents. Skin protecting agents comprise one or more agents that prevent the transmission of microbes (e.g., include antibacterial agents), skin cleansing agents (e.g. disinfectants and antiseptic agents) and sunscreen agents.

Skin cleansing agents used in the hair straightening formulations comprise sodium cocyl amino acids, benzalkonium chloride and/or centrimonium chloride. The skin protecting agent(s) generally comprises from about 0.1-10% by weight and preferably from about 0.5-5% by weight of the formulations.

Diluents

The term "diluent" as used herein refers to substances that may be used to dilute the active ingredient, the keratin protein fraction and keratin cross-linking agent. Water is the preferred diluent. The formulations require use of greater than 1% water to be effective. Advantageously, greater than five percent water is used, and more preferably, greater than 50%, and even more preferably, greater than 80% water is used. Alcohols such as ethyl alcohol and isopropyl alcohol may be used at low concentrations (about 0.5%) to enhance shaft penetration and reduce odor. High concentrations (about 35% and greater) of alcohols are not suitable as they disrupt the effectiveness of the formulations.

Auxiliary Ingredients

The hair straightening formulations also comprise one or more thickeners, particularly, when the formulation is in the form of a cream, lotion or gel. Such thickeners comprise polyethylene glycol and/or sodium polyacrylate. The thickener(s) may be present in an amount of about 0.1-5% by weight and more preferably in the amount of about 0.2-1% by weight.

Fragrances may also be added to mask the odor of various other components in the formulation of the present invention. Examples of such fragrances include but are not limited to caramel, vanilla. The thickener(s) may be present in an amount of about 0.1-10% by weight and more preferably in the amount of about 0.5-5% by weight.

Hair Straightening Systems and their Uses

The invention relates to hair straightening and conditioning systems.

System #1

The systems include a hair relaxer (e.g., shampoo), hair fixative, natural compounds, a skin protectant, and heat and afford a prolonged period (months after only one use despite frequent hair washings) of hair straightening. The systems are suitable for home use due to their ease of use and low potential for skin irritation or damage to the hair.

The systems can ideally be used as follows (with modifications as seen fit):

1. Hair Relaxer: Wash hair with a salt-free clarifying shampoo having a pH of 7-8. This product will swell and open the cuticle and make it semi-porous due to the breakage of the disulfide bonds.

2. Scalp Protectant: Coat and gently rub the scalp with a thin film of cellulose sulfate gel using a small hand-held applicator or fingers. The cellulose sulfate is applied as a gel (alkaline pH at 9-10) to the scalp in concentrations ranging from 0.5%-5% with a preferred concentration of 2-3%.

3. Hair Fixative: Allow hair to dry (can use a blow-dryer) but while slightly wet, apply the acidic glyoxal fixative (the hair after the fixative and the heating will have a pH of approximately 2 to 4) that contains keratin and epigallocatechin gallate along with other ingredients (as noted in the ingredient list below) in about one inch sections of hair (¼ inches from scalp) using a brush and comb. Blow dry into the hair until dry.

4. Heat: Use a hot comb or iron up to a maximum temperature of 450 degrees Fahrenheit. Use in ½ inch sections with 10 strokes of combing per section.

5. Do not wash hair for 24-48 hours.

Hair Relaxer

A shampoo that is slightly basic (pH of 7-8) and containing citric acid (buffered with sodium citrate) can be used to relax the hair. The slightly alkaline pH swells the hair and breaks down the disulfide double bond of the cysteine portion of the keratin molecule. In addition, the porosity of the cuticle layer (the outer layer of the hair) is important since it determines the amount of treatment (fixative) agent which can subsequently enter the cortex of the hair.

Hair Fixative

After the hair is relaxed, the fixative is used to cross-link and reform the keratin molecule, forming a stable structure after it has been broken down by the relaxer. The fixative to accomplish this should be an agent that cross-links the keratin bonds. In this particular embodiment, the keratin cross-linking agent comprises a nonformaldehyde aldehyde, more particularly a dialdehyde and even more particularly, glyoxal.

The hair fixative preparation contains hydrolyzed keratin and epigallocatechin gallate as the other main active ingredients. It has been found that the use of particular natural compounds in predetermined proportions achieves a straightening effect while simultaneously conditioning the hair. Among the primary components of the subject are keratin and epigallocatechin gallate that are in a mixture with other ingredients. Hydrolyzed protein is the superior conditioner for damaged hair because it can minimally penetrate the shaft and temporarily plug surface defects, resulting in hair with shine and a smooth feel. The protein should be hydrolyzed, as large protein molecules cannot penetrate the hair shaft. In addition, to our surprise, the addition of epigallocatechin gallate had an added benefit in increasing the conditioning of the hair and the length of time that the hair remained straight after multiple washes. The concentration of keratin in the preparation could range from 0.5% to 15% with a preferred range of 2%-8%. The concentration of the epigallocatechin gallate could range from 0.5% to 15% with a preferred range of 2%-10%.

Heat

A commercially available hot iron comb with a temperature maximum to 450 degrees Fahrenheit can be used to heat the hair after the application of the hair fixative.

System #2

Alternatively, one or more of the systems comprise (a) one of the hair straightening formulations; (b) one or more shampoos and (c) one or more conditioners. The hair straightening formulations are described hereinabove.

Shampoo

The shampoo is slightly basic (pH of 7-8), contains citric acid (buffered with sodium citrate) and can be used to relax the hair. The slightly alkaline pH swells the hair and breaks down the disulfide double bond of the cysteine portion of the keratin molecule. Furthermore, the shampoo is also salt free and/or paraben free. The shampoo may also contain sunscreen agents such as polysilicone-15.

One or more of the systems may in a particular embodiment comprise more than one type of shampoo. More particularly, the system may comprise at least one shampoo that modulates hair frizz, a defrizzing shampoo. In particular, the shampoo contains aloe, vitamin B, sunscreen and conditioners.

Conditioner

The systems comprise one or more conditioners to modulate moisture in hair. A conditioner is not intended to have a cleansing effect. The conditioners in one embodiment are sodium chloride free and/or paraben free and may also contain one or more sunscreens.

In a particular embodiment, the systems contain a rinse-off conditioner, a conditioner that is rinsed out of the hair after a certain period of time, e.g., range 2-4 minutes and/or a leave-in conditioner, a conditioner that is not rinsed from the hair. In a specific embodiment, leave in conditioner contains propylene glycol, panthal, cyclomethicone and tocopheryl acetate. Rinse off conditioner contains cetyl ester wax, amodimethicone and cetrimonium chloride. Both leave-in conditioner and rinse off conditioner may contain at least one of the following ingredients: (1) one or more humectants, (2) one or more proteins, (3) one or more acidifiers, (4) one or more thermal protectors; (5) dimethicone or cyclomethicone.

Methods for straightening hair using these hair straightening systems are provided. These methods comprise:

(a) Wash said hair with shampoo;

(b) Dry hair washed in step (a). Hair may be towel dried or dried with a blow dryer;

(c) The hair dried in step (b) may then be treated with a selected one of the disclosed hair straightening formulations. A comb is applied to the treated hair. The hair is treated for a sufficient amount of time to treat and ultimately obtain straightened hair. In a particular embodiment, the hair is treated for at least 0.25 minutes and in a more particular embodiment between 0.25-40 minutes.

(d) The treated hair of step (c) is subsequently dried by applying heat using the methods noted above (e.g., blow dryer). It is dried for a sufficient amount of time until it is dry and straight. This step may further comprise ironing the hair.

(e) The hair dried in step (d) is maintained (e.g. kept dry and straight) for at least 48 hours and in a particular embodiment not more than 96 hours to obtain maintained dried hair.

(f) The maintained dried hair of step (e) is washed with shampoo. In a particular embodiment, shampoo that modulates frizz in hair is used.

(g) The shampooing in step (f) is followed with conditioner for a time sufficient or effective to obtain conditioned hair. In a particular embodiment, a conditioner is applied to the hair for at least 0.2 minutes and in a more particular embodiment between about 0.2-4 minutes.

In another particular embodiment, a conditioner which modulates frizz in hair is used.

(h) The conditioned hair of step (g) is rinsed with water to obtain rinsed hair.

(i) The rinsed hair is treated with conditioner to obtain straightened hair. In a particular embodiment, the conditioner used is leave-in conditioner.

EXAMPLES

While not intended to limit in any way the scope of the present invention, the following examples demonstrate embodiments of the formulations and methods within the present invention. The use of the formulations hereinafter disclosed is not intended to be limited in any way by the characteristics of the hair tested in the following examples.

Example 1

Formulation #1

Hair Fixative Ingredient List Formulation:

| Ingredients | Weight % |
| --- | --- |
| Water | 76.00 |
| Glyoxal | 5.00 |
| Propylene Glycol | 4.00 |
| Keratin Protein Fraction | 3.00 |
| Epigallocatechin Gallate | 3.00 |
| Cetearyl Alcohol | 3.00 |
| Cetarimonium Chloride | 2.00 |
| Amondimethicone | 2.00 |
| Cyclopentasiloxane | 1.00 |
| Dimethicone | 0.50 |
| Fragrance | 0.50 |

Four clients were treated with the above formulation at a hair salon. The straightener was applied before using heat with a hot comb iron as described. The product was mixed thoroughly to produce a hair relaxing formulation in an emulsion form and allowed to dry. A hot iron comb with a wide-tooth comb as commonly used in the hair care business was used to evaluate the effects. The hair characteristics of the clients receiving the hair relaxing treatment were as follows: TEXTURE: Medium DENSITY: Thick/dense CURL PATTERN: Slightly wavy LENGTH: Above shoulder COLOR-TREATED: Permanent % OF GRAY: None PRIOR STRAIGHTENING None The dried straightened hair was evaluated with respect to the presence of electrostatic charge scatter at low humidity of about 40% Relative Humidity, 72 degree F. and at high humidity of about 80% Relative humidity, 72 degrees F. The straightener was tested using a blow dryer to evaluate the silkiness.

Analysis of the hair immediately after the hair relaxing treatment showed the hair was straightened in a satisfactory manner with minimal damage. All four clients stated that the hair felt less thick and heavy. The analysis of the hair (every two weeks for up to three months) after the hair relaxing treatment showed that the hair was in good condition, silky and straight, although it felt a bit dry and perceptively dry to the touch. No frizzing or curling was found up to 2 inches from the root of the hairs. Scatter and wind free-scatter response was tested to determine the silkiness and smoothness of the hair. The hair flow responded just like natural straight silky hair does. The conclusion was that the formulation with the addition of heat yields very good hair straightening and very little damage to the hair for a prolonged period of time.

Example 2

The hair straightening formulation may have the following composition:

| Substance | Weight % |
| --- | --- |
| Glyoxal 40% | 12.50% |
| Keratin Protein Fraction | 3.00% |
| Cetearyl Isononanoate | 2.00% |
| Ceteareth-20 | 1.75% |
| Cetearyl Alcohol | 3.00% |
| Glyceryl Stearate | 2.00% |
| Glycerin | 3.00% |
| Ceteareth 12 | 2.00% |
| Cetyl Palmitate | 2.00% |
| Cetrimonium Chloride | 1.50% |
| Amodimethicone | 5.00% |
| Cyclopentasiloxane | 2.00% |
| Dimethicone | 1.00% |
| Vanilla Extract | 0.60% |
| Sodium Polyacrylate | 0.40% |
| Caramel 10% Solution | 0.50% |
| Ethylhexylglycerin | 0.50% |
| Phenoxyethanol | 0.50% |
| Water | to 100% |

Example 3

Formulation #3

The formulation may have the following composition:

| Substance | Weight % |
| --- | --- |
| Purified water | to 100% |
| Propylene Glycol | 5.0% |
| Glycerin | 3.0% |
| Ceteareth-12 | 2.0% |
| Cetearyl Isononanoate | 2.0% |
| Ceteareth-20 | 1.75% |
| Centrimonium Chloride | 1.5% |
| Dimethicone | 1.0% |
| Vanilla Extract | 0.6% |
| Dimethiconol | 0.5% |
| Laureth 4 | 0.5% |
| Laureth-23 | 0.5% |
| Phenoxyethanol | 0.5% |
| Ethylhexylglycerin | 0.5% |
| Sodium Polyacrylate | 0.4% |
| Glyoxal | 0.35% |
| Hydrolyzed Keratin | 0.2% |
| Caramel | 0.15% |

The formulation is used as follows:
1. Hair is washed with shampoo provided.
2. The shampoo is rinsed from the hair and hair is subsequently blow-dried.
3. Treatment is applied to dry hair.
4. Treatment is applied to hair from root to end. The hair is saturated with the treatment and the hair is combed through.
5. The treatment is allowed to sit for 30 minutes.
6. Hair is dried with a blow dryer and subsequently ironed at high heat.
7. Hair is kept dry for 48 hours
8. After 48 hours, treatment is washed with De-frizz Shampoo and Conditioner
9. After 2 minutes of treatment with conditioner, conditioner is rinsed out with lukewarm water
10. The hair is optionally treated with Leave-In Conditioner.

Example 4

The formulation may have the following composition:

| Substance | Weight % |
| --- | --- |
| Purified water | to 100% |
| Dimethicone | 3.0% |
| Dimethiconol | 2.7% |

-continued

| Substance | Weight % |
|---|---|
| Sodium cocoyl aminoacids | 2.0% |
| Glyoxal | 1.3% |
| Potassium dimethicone PEG-7 panthenyl phosphate | 1.0% |
| Sodium Laneth-40 Maleate/Styrene Sulfonate copolymer | 0.5% |
| Phenoxyethanol | 0.5% |
| Ethylhexylglycerin | 0.5% |
| Laureth 4 | 0.3% |
| Laureth-23 | 0.3% |
| Hydrolyzed Keratin | 0.1% |

The formulation may be used as follows:
1. Hair is washed with shampoo
2. Shampoo is thoroughly rinsed from hair
3. Hair is towel dried.
4. Hair straightening treatment is sprayed on towel dried hair, and hair is subsequently combed through.
5. Treatment is allowed to sit for 30 minutes.
6. Hair is blow dried until completely dry and straight
7. Hair is ironed in small sections at high heat
8. Hair is kept dry and straight for 48 hours and optionally touched up with iron and/or blow dryer if necessary.
9. After 48 hours, treatment is washed out with shampoo followed by the De-Frizz Conditioner.
10. The De-frizz Conditioner is allowed to sit for 2 minutes.
11. After 2 minutes, conditioner is rinsed out with lukewarm water.
12. Hair may be further treated with Leave-In Conditioner.

Example 5

The formulation may have the following composition:

| Substance | Weight % |
|---|---|
| Purified water | to 100% |
| Dimethicone | 3.0% |
| Dimethiconol | 2.7% |
| Sodium cocoyl aminoacids | 2.0% |
| Glyoxal | 1.3% |
| Potassium dimethicone PEG-7 panthenyl phosphate | 1.0% |
| Sodium Laneth-40 Maleate/Styrene Sulfonate copolymer | 0.5% |
| Phenoxyethanol | 0.5% |
| Ethylhexylglycerin | 0.5% |
| Laureth 4 | 0.3% |
| Laureth-23 | 0.3% |
| Hydrolyzed Keratin | 0.6% |

The formulation may be used as follows:
1. Hair is washed with shampoo
2. Shampoo is thoroughly rinsed from hair
3. Hair is towel dried.
4. Hair straightening treatment is sprayed on towel dried hair, and hair is subsequently combed through.
5. Treatment is allowed to sit for 30 minutes.
6. Hair is blow dried until completely dry and straight
7. Hair is ironed in small sections at high heat
8. Hair is kept dry and straight for 48 hours and optionally touched up with iron and/or blow dryer if necessary.
9. After 48 hours, treatment is washed out with shampoo followed by the De-Frizz Conditioner.
10. The De-frizz Conditioner is allowed to sit for 2 minutes.
11. After 2 minutes, conditioner is rinsed out with lukewarm water.
12. Hair may be further treated with Leave-In Conditioner.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties

What is claimed is:

1. A hair straightening formulation consisting of:
    12.50 weight % of Glyoxal (40%);
    3.00 weight % of keratin protein fraction;
    2.00 weight % of cetearyl isononanoate;
    1.75 weight % of Ceteareth-20;
    3.00 weight % of cetearyl alcohol;
    2.00 weight % of glyceryl stearate;
    3.00 weight % of glycerin;
    2.00 weight % of Ceteareth 12;
    2.00 weight % of cetyl palmitate;
    1.50 weight % of cetrimonium chloride;
    5.00 weight % of amodimethicone;
    2.00 weight % of cyclopentasiloxone;
    1.00 weight % of dimethicone;
    0.60 weight % of vanilla extract;
    0.40 weight % of sodium polyacrylate;
    0.50 weight % of caramel (10% solution);
    0.50 weight % of ethylhexylglycerin;
    0.50 weight % of phenoxyethanol; and
    water.

2. A hair straightening formulation consisting of:
    5.0 weight % of propylene glycol;
    3.0 weight % of glycerin;
    2.0 weight % of Ceteareth-12;
    2.0 weight % of cetearyl isononanoate;
    1.75 weight % of Ceteareth-20;
    1.5 weight % of centrimonium chloride;
    1.0 weight % of dimethicone;
    0.6 weight % of vanilla extract;
    0.5 weight % of dimethiconol;
    0.5 weight % of Laureth 4;
    0.5 weight % of Laureth-23;
    0.5 weight % of phenoxyethanol;
    0.5 weight % of ethylhexylglycerin;
    0.4 weight % of sodium polyacrylate;
    0.35 weight % of glyoxal;
    0.2 weight % of hydrolyzed keratin;
    0.15 weight % of caramel; and
    purified water.

3. A hair straightening formulation consisting of:
    3.0 weight % of dimethicone;
    2.7 weight % of dimethiconol;
    2.0 weight % of sodium cocoyl aminoacids;
    1.3 weight % of glyoxal;
    1.0 weight % of potassium dimethicone PEG-7 panthenyl phosphate;
    0.5 weight % of Sodium Laneth-40 Maleate/Styrene Sulfonate copolymer;
    0.5 weight % of phenoxyethanol;
    0.5 weight % of ethylhexylglycerin;
    0.3 weight % of Laureth 4;
    0.3 weight % of Laureth-23;
    0.1 weight % of hydrolyzed keratin; and
    purified water.

4. A hair straightening formulation consisting of:
3.0 weight % of dimethicone;
2.7 weight % of dimethiconol;
2.0 weight % of sodium cocoyl aminoacids;
1.3 weight % of glyoxal;
1.0 weight % of potassium dimethicone PEG-7 panthenyl phosphate;
0.5 weight % of Sodium Laneth-40 Maleate/Styrene Sulfonate copolymer;
0.5 weight % of phenoxyethanol;
0.5 weight % of ethylhexylglycerin;
0.3 weight % of Laureth 4;
0.3 weight % of Laureth-23;
0.6 weight % of hydrolyzed keratin; and
purified water.

* * * * *